US012640252B2

(12) United States Patent
Neumann

(10) Patent No.:  US 12,640,252 B2
(45) Date of Patent:  May 26, 2026

(54) SYSTEMS AND METHODS FOR PRODUCING A HOMEOPATHIC PROGRAM FOR MANAGING GENETIC DISORDERS

(71) Applicant: KPN INNOVATIONS, LLC., Lakewood, CO (US)

(72) Inventor: Kenneth Neumann, Lakewood, CO (US)

(73) Assignee: KPN INNOVATIONS, LLC, Lakewood, CO (US)

( * ) Notice: Subject to any disclaimer, the term of this patent is extended or adjusted under 35 U.S.C. 154(b) by 1089 days.

(21) Appl. No.: 17/464,011

(22) Filed: Sep. 1, 2021

(65) Prior Publication Data

US 2022/0208348 A1  Jun. 30, 2022

Related U.S. Application Data

(63) Continuation-in-part of application No. 17/136,151, filed on Dec. 29, 2020, now Pat. No. 11,145,401.

(51) Int. Cl.
G16H 20/60  (2018.01)
G16B 40/00  (2019.01)
(Continued)

(52) U.S. Cl.
CPC ............. G16H 20/60 (2018.01); G16B 40/00 (2019.02); G16H 10/40 (2018.01); G16H 20/90 (2018.01);
(Continued)

(58) Field of Classification Search
CPC ........ G16H 50/30; G16H 70/60; G16H 50/20; G16B 50/00; G16B 50/30; G16B 20/00
(Continued)

(56) References Cited

U.S. PATENT DOCUMENTS

| 10,515,448 B2 * | 12/2019 | Fetzer | .................... | G06V 40/11 |
| 10,734,105 B1 * | 8/2020 | Neumann | .............. | G16H 50/20 |

(Continued)

FOREIGN PATENT DOCUMENTS

| CH | 713713 A2 | 10/2018 |
| CH | 713714 A2 | 10/2018 |

(Continued)

OTHER PUBLICATIONS

Arkadiano et al. , Improved weight management using genetic information to personalize a calorie controlled diet, Dec. 31, 2007.

(Continued)

*Primary Examiner* — Dilek B Cobanoglu
(74) *Attorney, Agent, or Firm* — Caldwell LLC

(57) ABSTRACT

A system for generating a sustenance plan for managing genetic disorders is disclosed. The system includes a computing device. The computing device is configured to receive an input which may include genetics test data. The computing device is configured to identify a plurality of biological indices of a disease state as a function of the genetics test data. The plurality of biological indices comprises at least one biological index related to a genetic disease state. The computing device is configured to generate a genetic disorder classifier. The computing device is configured to produce a homeopathic program as a function of the genetic disorder. A method for producing a homeopathic program for managing genetic disorders is disclosed.

16 Claims, 8 Drawing Sheets

(51) Int. Cl.

| | | |
|---|---|---|
| *G16H 10/40* | (2018.01) | |
| *G16H 20/90* | (2018.01) | |
| *G16H 50/20* | (2018.01) | |
| *G16H 50/30* | (2018.01) | |
| *G16H 50/70* | (2018.01) | |

(52) U.S. Cl.
CPC ............. *G16H 50/20* (2018.01); *G16H 50/30* (2018.01); *G16H 50/70* (2018.01)

(58) Field of Classification Search
USPC .......................................... 703/11; 705/2, 3
See application file for complete search history.

(56) References Cited

U.S. PATENT DOCUMENTS

| | | | |
|---|---|---|---|
| 11,393,589 B2* | 7/2022 | Neumann ............... | G16H 10/60 |
| 11,756,655 B2* | 9/2023 | Eltoukhy ............... | G16H 50/30 |
| | | | 703/11 |
| 2007/0196841 A1 | 8/2007 | Ruano et al. | |
| 2008/0221932 A1 | 9/2008 | Kane et al. | |
| 2008/0275912 A1 | 11/2008 | Roberts et al. | |
| 2008/0317733 A1 | 12/2008 | Azimi | |
| 2010/0042438 A1 | 2/2010 | Moore et al. | |
| 2010/0070455 A1 | 3/2010 | Halperin et al. | |
| 2010/0105038 A1 | 4/2010 | Draper et al. | |
| 2010/0153016 A1 | 6/2010 | Stefanon et al. | |
| 2010/0191735 A1* | 7/2010 | Reiss ..................... | G16B 50/00 |
| | | | 435/375 |
| 2011/0159489 A1 | 6/2011 | Sancak | |
| 2012/0277180 A1 | 11/2012 | Marini et al. | |
| 2013/0151270 A1* | 6/2013 | Nova ..................... | G16H 50/20 |
| | | | 705/2 |
| 2015/0379193 A1* | 12/2015 | Bassett, Jr. ........... | G16B 20/00 |
| | | | 702/19 |
| 2016/0140288 A1 | 5/2016 | Kuan et al. | |
| 2016/0253770 A1* | 9/2016 | Downs ................... | G16B 40/00 |
| | | | 705/3 |
| 2017/0268057 A1 | 9/2017 | Tranah et al. | |
| 2018/0294047 A1* | 10/2018 | Hosseini ................ | G16B 50/30 |
| 2021/0343414 A1* | 11/2021 | Robinson .............. | G16H 50/30 |
| 2022/0093252 A1* | 3/2022 | Molony ................. | G16H 70/60 |

FOREIGN PATENT DOCUMENTS

| | | | | |
|---|---|---|---|---|
| CN | 104651485 A | | 5/2015 | |
| RU | 2691145 C2 | | 6/2019 | |
| WO | 2019074388 | | 4/2019 | |
| WO | WO-2019183122 A1 * | | 9/2019 | ............ G06N 20/20 |

OTHER PUBLICATIONS

Maglio et al. , The PNPLA3 I148M variant and chronic liver disease: When a genetic mutation meets nutrients, Dec. 31, 2007.

* cited by examiner

600

605
Receive Input

610
Identify Plurality of Biological Indices

615
Generate a Genetic Disorder Classifier

620
Classify at least One Biological Index and at least one Genetic Marker to a Positive Result for a Genetic Disorder 625
General Alimentary Plan

700

705
Receive Input

710
Identify Plurality of Biological Indices

715
Generate a Genetic Disorder Classifier

720
Classify at least One Biological Index and at least one Genetic Marker to a Positive Result for a Genetic Disorder 725
Produce a Homeopathic Program

1

SYSTEMS AND METHODS FOR PRODUCING A HOMEOPATHIC PROGRAM FOR MANAGING GENETIC DISORDERS

CROSS-REFERENCE TO RELATED APPLICATIONS

This application is a continuation-in-part of Non-provisional application Ser. No. 17/136,151 filed on Dec. 29, 2020 and entitled "SYSTEMS AND METHODS FOR GENERATING A SUSTENANCE PLAN FOR MANAGING GENETIC DISORDERS," the entirety of which is incorporated herein by reference.

FIELD OF THE INVENTION

The present disclosure generally relates to the field of nutrition for disease management. In particular, the present invention is directed to a system and method for producing a homeopathic program for managing genetic disorders.

BACKGROUND

Nutrition is an essential function of life as it provides the necessary nutrients the body needs to sustain all functions of life. The use of artificial intelligence in the field of nutrition may assist in the development and management of a healthy lifestyle for an individual.

SUMMARY OF THE DISCLOSURE

In an aspect of the disclosure, a system for producing a homeopathic program is disclosed. A system for producing a homeopathic program for managing genetic disorders includes a computing device configured to receive at least one genetic marker and an input comprising genetics test data, identify a plurality of biological indices of a disease state as a function of the genetics test data, wherein the plurality of biological indices comprises at least one biological index related to a genetic disease state, generate a genetic disorder classifier, wherein the generating the genetic disorder classifier comprises receiving genetic disorder training data correlating biological indices of genetic disorders and genetic markers to genetic disorder labels, and training the genetic disorder classifier using the genetic disorder training data, input the at least one biological index and the at least one genetic marker into the genetic disorder classifier, classify, using the genetic disorder classifier, the at least one biological index and the at least one genetic marker to a positive result for a genetic disorder, and produce a homeopathic program as a function of the genetic disorder, wherein producing the homeopathic program further comprises receiving a homeopathic guideline, and producing the homeopathic program as a function of the homeopathic guideline and the genetic disorder.

In another aspect of the disclosure, a method for generating a homeopathic program for managing genetic disorders is disclosed. A method for generating a homeopathic program for managing genetic disorders includes receiving, by a computing device, at least one genetic marker and an input comprising genetics test data, identifying, by the computing device, a plurality of biological indices of a disease state as a function of the genetics test data, wherein the plurality of biological indices comprises at least one biological index related to a genetic disease state, generating, by the computing device, a genetic disorder classifier, wherein the generating the genetic disorder classifier comprises receiving genetic disorder training data correlating biological indices of genetic disorders and genetic markers to genetic disorder labels, and training the genetic disorder classifier using the genetic disorder training data, inputting, by the computing device, the at least one biological index and the at least one genetic marker into the genetic disorder classifier, classifying, by the computing device, using the genetic disorder classifier, the at least one biological index and the at least one genetic marker to a positive result for a genetic disorder, and producing, by the computing device, a homeopathic program as a function of the genetic disorder, wherein producing the homeopathic program further comprises receiving a homeopathic guideline, and producing the homeopathic program as a function of the homeopathic guideline and the genetic disorder.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for generating a homeopathic program for managing genetic disorders. The system may include a computing device that may receive an input which may be in the form of a biochemical generic test. The input may include genetic test data which may be used in identifying biological indices related to a genetic disorder. A classifier is trained and used to classify at least one biological index of a genetic disorder and genetic markers to a positive result indicating the presence of a genetic disorder. A positive result may produce a homeopathic program to treat and/or prevent the genetic disorder.

A practical application of this technology includes the use of a machine-learning model to provide a user access to alimentary plans that may improve a genetic disorder. The system and method may analyze the progression of the genetic disorder as measured by the presence or absence of the biological index. The machine-learning model may also be train to output other disease states that may be related to the genetic disorder. The system and method allow for an update of the alimentary plan if the genetic disorder continues to progress.

Figure 1:
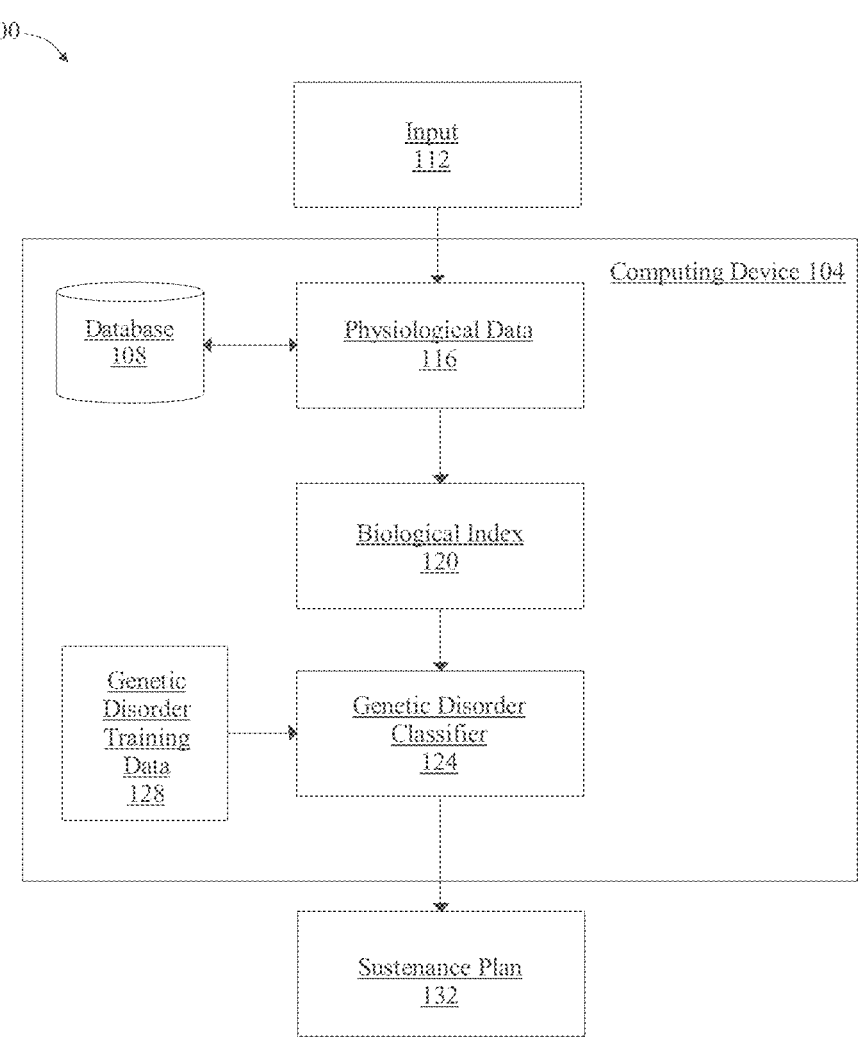
FIG. 1 is a block diagram of an exemplary embodiment of a system of determining a sustenance plan for managing a genetic disorder.

Referring now to FIG. 1, an exemplary embodiment of a system 100 for generating an alimentary plan for managing a skin disorder is illustrated. System includes a computing device 104. Computing device 104 may include any computing device as described in this disclosure, including without limitation a microcontroller, microprocessor, digital signal processor (DSP) and/or system on a chip (SoC) as described in this disclosure. Computing device 104 may include, be included in, and/or communicate with a mobile device such as a mobile telephone or smartphone. Computing device 104 may include a single computing device operating independently, or may include two or more computing device operating in concert, in parallel, sequentially or the like; two or more computing devices may be included together in a single computing device or in two or more computing devices. Computing device 104 may interface or communicate with one or more additional devices as described below in further detail via a network interface device. Network interface device may be utilized for connecting a computing device to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Computing device 104 may include but is not limited to, for example, a computing device or cluster of computing devices in a first location and a second computing device or cluster of computing devices in a second location. Computing device 104 may include one or more computing devices dedicated to data storage, security, distribution of traffic for load balancing, and the like. Computing device 104 may distribute one or more computing tasks as described below across a plurality of computing devices of computing device, which may operate in parallel, in series, redundantly, or in any other manner used for distribution of tasks or memory between computing devices. Computing device 104 may be implemented using a "shared nothing" architecture in which data is cached at the worker, in an embodiment, this may enable scalability of system 100 and/or computing device.

With continued reference to FIG. 1, computing device 104 may be designed and/or configured to perform any method, method step, or sequence of method steps in any embodiment described in this disclosure, in any order and with any degree of repetition. For instance, Computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Still referring to FIG. 1, computing device 104 may connect to and/or include a database 108. Database 108 may be implemented, without limitation, as a relational database 108, a key-value retrieval database 108 such as a NOSQL database 108, or any other format or structure for use as a database 108 that a person skilled in the art would recognize as suitable upon review of the entirety of this disclosure. Database 108 may alternatively or additionally be implemented using a distributed data storage protocol and/or data structure, such as a distributed hash table or the like. Database 108 may include a plurality of data entries and/or records as described above. Data entries in a database 108 may be flagged with or linked to one or more additional elements of information, which may be reflected in data entry cells and/or in linked tables such as tables related by one or more indices in a relational database 108. Persons skilled in the art, upon reviewing the entirety of this disclosure, will be aware of various ways in which data entries in a database 108 may store, retrieve, organize, and/or reflect data and/or records as used herein, as well as categories and/or populations of data consistently with this disclosure. In some embodiments, network data, or other information such as user information, transfer party information, and alimentary provider information, may be stored in and/or retrieved from database 108.

Figure 2:
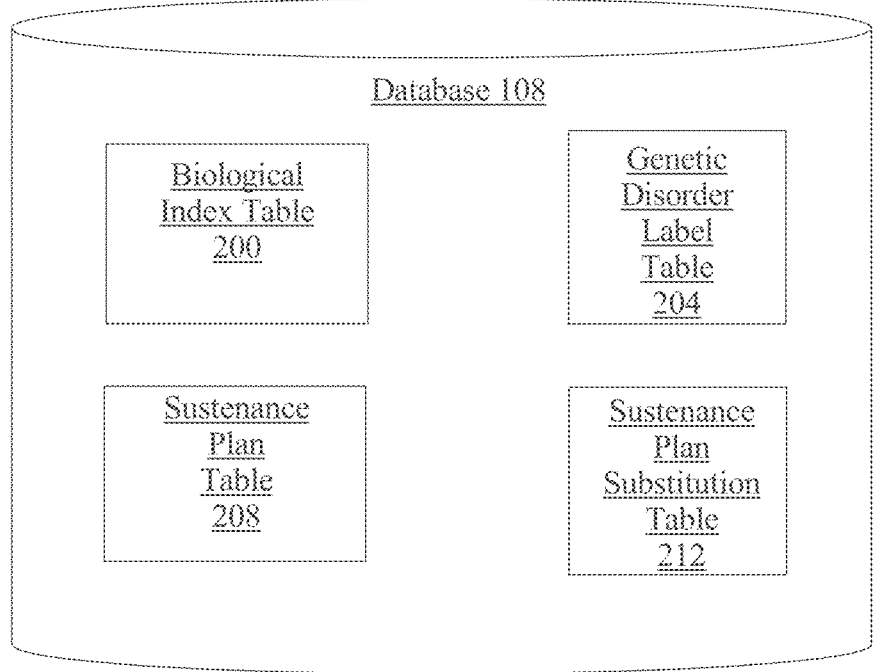
FIG. 2 is a block diagram of an exemplary embodiment of a database.

Referring now to FIG. 2 an exemplary embodiment of a database 108 is illustrated. Database 108 may, as a non-limiting example, organize data stored in the database according to one or more database tables. One or more database tables may be linked to one another by, for instance, common column values. For instance, a common column between two tables of database 108 may include an identifier of alimentary providers, for instance as defined below; as a result, a query may be able to retrieve all rows from any table pertaining to a given alimentary provider. Other columns may include any other category usable for organization or subdivision of data, including types of data, common pathways between, for example, an alimentary combination and a first alimentary provider, or the like; persons skilled in the art, upon reviewing the entirety of this disclosure, will be aware of various ways in which expert data from one or more tables may be linked and/or related to expert data in one or more other tables.

Still referring to FIG. 2, one or more database tables in database 108 may include, as a non-limiting example, a biological index table 200. Biological index table 200 may be used to store biological indices corresponding to genetic disorders, biological indices that correspond to related disease states, or the like. As another non-limiting example, one or more tables in database 108 may include a genetic disorder label table 204. Genetic disorder label table 204 may be used to store correlations between biological indices and potential genetic disorders, and the like. Another non-limiting example, one or more tables in database 108 may include a sustenance plan table 208. A sustenance plan table 208 may include, but not limited to sustenance combinations that may treat or prevent a specific genetic disorder, adverse foods affecting genetic disorders, and the like. As another non-limiting example, one or more tables in database 108 may be a sustenance plan substitution table. A sustenance plan substitution table 212 may include sustenance combinations that may include allowable substitutions for sustenance combinations, substitutions that may create an adverse effect on a genetic disorder, and the like.

Referring back to FIG. 1, computing device 104 receives input 112. Input 112 includes genetic test data 116, where genetic test data 116 includes data from a biochemical genetic test. An "input," as used in this disclosure, may include, but not limited to any medical test, a user's health assessment, a user's nutritional assessment, an assessment conducted in any website related to a genetic disorder, a direct entry from a user, and the like. As used in this disclosure, "genetic test data" is any data indicative of a person's genetic state; genetic state may be evaluated about one or more measures of health of a person's body, one or more systems within a person's body such as a circulatory system, a digestive system, a nervous system, or the like, one or more organs within a person's body, and/or any other subdivision of a person's body useful for diagnostic or prognostic purposes. For instance, and without limitation, a particular set of biomarkers, test results, and/or biochemical information may be recognized in a given medical field as useful for identifying various disease conditions or prognoses within a relevant field. For instance, and without limitation, genetics test data 116 may include genomic data, including deoxyribonucleic acid (DNA) samples and/or sequences, such as without limitation DNA sequences contained in one or more chromosomes in human cells. Genomic data may include, without limitation, ribonucleic acid (RNA) samples and/or sequences, such as samples and/or sequences of messenger RNA (mRNA) or the like taken from human cells. Genetic data may include telomere lengths. Genomic data may include epigenetic data including data describing one or more states of methylation of genetic material. Genetics test data 116 may include proteomic data, which as used herein is data describing all proteins produced and/or modified by an organism, colony of organisms, or system of organisms, and/or a subset thereof. Genetics test data may include data concerning a microbiome of a person, which as used herein includes any data describing any microorganism and/or combination of microorganisms living on or within a person, including without limitation biomarkers, genomic data, proteomic data, and/or any other metabolic or biochemical data useful for analysis of the effect of such microorganisms on other physiological state data of a person, and/or on prognostic labels and/or ameliorative processes as described in further detail below. With continued reference to FIG. 1, genetics test data 116 may include, without limitation any result of any medical test, physiological assessment, cognitive assessment, psychological assessment, nutritional, or the like. For instance, a user may have completed a nutritional assessment that may determine the nutritional behaviors and patterns of a user. Nutritional behaviors and patterns may include, but are not limited to, types of foods the user likes and/or dislikes; preferred beverages consumed with the types of foods; preferred consumption schedule; preferred substitutions for the types of foods a user likes; foods that may make the user feel unwell; known food allergies, such as a peanut allergy; known food illnesses, such as, but not limited to lactose intolerance; the general health condition of the user, and the like. In an embodiment, based on the nutritional assessment from the user, computing device 104 may output an adverse effect of nutrition on the genetic disorder. For instance, a nutritional assessment may include a favorite type of food such as green vegetables which may include kale or broccoli. As a single gene, TAS2R38, may be responsible for a user's ability to taste phenylthiocarbamide contained in such green vegetables. Computing device 104 may output that those types of vegetables may be tasteless or very bitter as a result of a genetic disorder where TAS2R38 is missing or express incorrectly. The absorption of certain vitamins can also be affected by genetics, such as increased iron absorption in hemochromatosis, a disorder where the body's iron levels build up and overload. people with hemochromatosis possess a gene variant on the short arm of chromosome 6, which is linked to HLA Locus A, and which allows increased iron absorption. A user preferring to eat red meat or raw seafood may be cautioned that consumption of such foods may have an adverse impact on hemochromatosis, if a user has been diagnosed with such disorder. Input 112 may include at least a genetic test data 116 from one or more other devices after performance; system 100 may alternatively or additionally perform one or more assessments and/or tests to obtain at least a genetic test data 116, and/or one or more portions thereof, on system 100. For instance, at least genetics test data 116 may include or more entries by a user in a form or similar graphical user interface object; one or more entries may include, without limitation, user responses to questions on a psychological, behavioral, personality, or cognitive test. For instance, at least a computing device 104 may present to user a set of assessment questions designed or intended to evaluate a current state of mind of the user, a current psychological state of the user, a personality trait of the user, or the like; at least a computing device 104 may provide user-entered responses to such questions directly as at least a genetic test data 116 and/or may perform one or more calculations or other algorithms to derive a score or other result of an assessment as specified by one or more testing protocols, such as automated calculation of a Stanford-Binet and/or Wechsler scale for IQ testing, a personality test scoring such as a Myers-Briggs test protocol, or other assessments that may occur to persons skilled in the art upon reviewing the entirety of this disclosure.

With continued reference to FIG. 1, assessment and/or self-assessment data, and/or automated or other assessment results, obtained from a third-party device; third-party device may include, without limitation, a server or other device (not shown) that performs automated cognitive, psychological, behavioral, personality, or other assessments. Third-party device may include a device operated by an informed advisor. An informed advisor may include any medical professional who may assist and/or participate in the medical treatment of a user. An informed advisor may include a medical doctor, nurse, physician assistant, pharmacist, yoga instructor, nutritionist, spiritual healer, meditation teacher, fitness coach, health coach, life coach, and the like.

With continued reference to FIG. 1, user body measurements may be related to particular dimensions of the human body. A "dimension of the human body" as used in this disclosure, includes one or more functional body systems that are impaired by disease in a human body and/or animal body. Functional body systems may include one or more body systems recognized as attributing to root causes of disease by functional medicine practitioners and experts. A "root cause" as used in this disclosure, includes any chain of causation describing underlying reasons for a particular disease state and/or medical condition instead of focusing solely on symptomatology reversal. Root cause may include chains of causation developed by functional medicine practices that may focus on disease causation and reversal. For instance and without limitation, a medical condition such as diabetes may include a chain of causation that does not include solely impaired sugar metabolism but that also includes impaired hormone systems including insulin resistance, high cortisol, less than optimal thyroid production, and low sex hormones. Diabetes may include further chains of causation that include inflammation, poor diet, delayed food allergies, leaky gut, oxidative stress, damage to cell membranes, and dysbiosis. Dimensions of the human body may include but are not limited to epigenetics, gut-wall, microbiome, nutrients, genetics, and/or metabolism.

With continued reference to FIG. 1, epigenetic, as used herein, includes any user body measurements describing changes to a genome that do not involve corresponding changes in nucleotide sequence. Epigenetic body measurement may include data describing any heritable phenotypic. Phenotype, as used herein, include any observable trait of a user including morphology, physical form, and structure. Phenotype may include a user's biochemical and physiological properties, behavior, and products of behavior. Behavioral phenotypes may include cognitive, personality, and behavior patterns. This may include effects on cellular and physiological phenotypic traits that may occur due to external or environmental factors. For example, DNA methylation and histone modification may alter phenotypic expression of genes without altering underlying DNA sequence. Epigenetic body measurements may include data describing one or more states of methylation of genetic material.

Additionally, and with continued reference to FIG. 1, genetics test data 116 may include data from a biochemical genetic test. As used in this disclosure, a "biochemical genetic test" is a test that includes a study of enzymes and proteins, chromosomes, and genes where the function of the enzymes and proteins, chromosomes, and genes may be abnormal. In one embodiment, genetics test data 116 may include results of a diagnostic genetic testing which, as used in this disclosure, may be used to identify or discard a specific genetic or chromosomal disorder. The specific genetic or chromosomal disorder may be suspected based on physical symptoms or signs. Diagnostic genetic testing may be performed at any time in a person's life which may include in utero. Additionally, biochemical genetic testing may be performed, for instance but not limited to, a blood sample, a urine sample, spinal fluid, amniotic fluid, or in any tissue sample. One example of biochemical genetic testing methods includes molecular genetic testing. Molecular genetic testing includes testing a single gene or short strands of DNA to identify at least one variation or at least one mutation that may lead to a generic disorder. Techniques used in molecular genetic testing include, but are not limited to, a polymerase chain reaction test ("PCR"), DNA sequencing, microarray testing, gene expression profiling, and the like. Another example of a biochemical genetic testing method may include chromosomal genetic testing. Chromosomal genetic testing analyzes whole chromosomes or long strands of DNA to check for large genetic changes, which may include, but are not limited to, an extra copy of a chromosome that may lead to a genetic disorder. Techniques used in chromosomal genetic testing include but are not limited to cytogenetics which may include karyotyping and fluorescence in situ hybridization ("FISH"). A further example of a biochemical genetic testing methods may include the use of immunoassays in the detection of a genetic disorder. Immunoassays are tests based on a very specific binding that occurs between an immunoglobulin or an antibody—a protein produced by the immune system to recognize, bind to, and neutralize a foreign substance in the body—and the substance that it specifically recognizes, such as the foreign substance or an antigen, in the, for example, blood, urine, spinal, or amniotic fluid sample. Combinations of the above-referenced techniques may be used to detect genetic disorders. As a non-limiting illustrative example, an immunoassay for detecting a specific genetic syndrome may be combined with genotyping on a DNA chain amplified with the use of PCR to detect an abnormal sequence that may result in a genetic disorder.

With continued reference to FIG. 1, computing device 104 identifies a plurality of biological indices 120 based on the genetics test data. Plurality of biological indices 120 includes at least one biological index related to a disease state. A "disease state" as used in this disclosure, includes any harmful deviation from the normal structural and/or function state of a human being. A disease state may include any medical condition and may be associated with specific symptoms and signs. A disease state may be classified into different types including infectious diseases, deficiency diseases, hereditary diseases, and/or physiological diseases. For instance, and without limitation, internal dysfunction of the immune system may produce a variety of different diseases including immunodeficiency, hypersensitivity, allergies, and/or autoimmune disorders. The disease state includes at least one genetic disorder. A "genetic disease state," as used in this disclosure, is a disease state that involves any mutation or change of a user that may adversely affect the user and cause a genetic disorder. As used in this disclosure, a "genetic disorder" is a disease state caused in whole or in part by a change in the DNA sequence away from the normal sequence. Genetic disorders may be caused by a mutation in one gene (monogenic disorder), by mutations in multiple genes (multifactorial inheritance disorder), by a combination of gene mutations and environmental factors, or by damage to chromosomes (changes in the number or structure of entire chromosomes, the structures that carry genes). Examples related to genetic disorders may include hemophilia A, where the gene responsible for producing factor VIII is mutated. This mutation, for example, would affect the ability for a user's blood to clot. Another example may include a disease state such as Down Syndrome. A user with Down Syndrome has extra material from chromosome no. 21 which cause a change in the development of the embryo resulting in potential physical and mental abnormalities. The most common error in chromosome replication is "trisomy 21", where the new cell gets three copies of chromosome 21, instead of two. Additionally, a "biological index," as used in this disclosure, is a biological entity found in any body fluid, for example blood, skin sample, or the like, that indicates the presence or absence of a disorder or a disease. A biological index may be classified as, for example, a monitoring biological indicator. A "monitoring biological indicator," as used in this specification, is a biological index that may be used to assess the progress of a disease or to monitor the effects of a therapeutic agent, such as, for example, a platelet-rich plasma treatment. In another example, a biological index may be a diagnostic biological index. A "diagnostic biological index," as defined in this disclosure is a biological index that is used to detect the presence of a disease or a disorder of interest. In an embodiment, the plurality of biological index comprises a diagnostic indicator. Another example of a biological index is a predictive biological index. A "predictive biological index," as used in this disclosure, is a biological indicator used to predict what group of patients will respond favorably or unfavorably to a particular treatment. Examples of biological index that may be used in diagnosing a genetic disorder may include but are not limited to Receptor tyrosine Kinase (9RTK), FGFR-3, EGFR<ERBB2, HER2, ERBB3, NMDA receptor upregulation, repressive H3K9me2, EHMT1, CRIN1, and the like.

Alternatively or additionally, and with continued reference to FIG. 1, in an embodiment, computing device 104 may be configured to analyze a progression of the genetic disorder as a function of the at least one biological index. For instance, a potential underlying genetic cause of Duchenne Muscular Dystrophy ("DMD") may be the presence of a variety of DMD gene mutations that result in dystrophin reduction or absence in skeletal muscle. Using a technique such as microarray-based expression profiling to identify and quantitate the levels of dystrophin in skeletal tissue, computing device 104 may analyze the levels of dystrophin in a control sample and a tissue sample. By comparing the levels of the biological index, dystrophin in this case, between the control sample and the actual tissue sample, a diagnosis and/or progression of a disease, such as DMD may be determined. Similarly, a plurality of biological indices may be analyzed using microarray-based expression profiling or other techniques where their presence and/or absence may determine a diagnosis for the disease or, if the test is positive for a disease, how far has the diseased progress.

Still referring to FIG. 1, computing device 104 may generate a genetic disorder classifier 124. Computing device 104 may generate genetic disorder classifier 124 by receiving genetic disorder training data 128. "Training data," as used herein, is data containing correlations that a machine-learning process may use to model relationships between two or more categories of data elements. For instance, and without limitation, training data such as genetic disorder training data 128 may include a plurality of data entries, each entry representing a set of data elements that were recorded, received, and/or generated together; data elements may be correlated by shared existence in a given data entry, by proximity in a given data entry, or the like. Multiple data entries in training data 128 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 128 according to various correlations; correlations may indicate causative and/or predictive links between categories of data elements, which may be modeled as relationships such as mathematical relationships by machine learning processes as described in further detail below. Training data 128 may be formatted and/or organized by categories of data elements, for instance by associating data elements with one or more descriptors corresponding to categories of data elements. As a non-limiting example, training data 128 may include data entered in standardized forms by persons or processes, such that entry of a given data element in a given field in a form may be mapped to one or more descriptors of categories. Elements in training data 128 may be linked to descriptors of categories by tags, tokens, or other data elements; for instance, and without limitation, training data 128 may be provided in fixed-length formats, formats linking positions of data to categories such as comma-separated value (CSV) formats and/or self-describing formats such as extensible markup language (XML), enabling processes or devices to detect categories of data.

Alternatively or additionally, and with continued reference to FIG. 1, training data 128 may include one or more elements that are not categorized; that is, training data 128 may not be formatted or contain descriptors for some elements of data. Machine learning algorithms and/or other processes may sort training data 128 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine learning algorithms, and/or automated association of data in the data entry with descriptors or into a given format. The ability to categorize data entries automatedly may enable the same training data 128 to be made applicable for two or more distinct machine learning algorithms as described in further detail below. Training data 128 used by computing device 104 may correlate any input data as described in this disclosure to any output data as described in this disclosure. Training data may contain entries, each of which correlates a machine learning process input to a machine learning process output, for instance without limitation, one or more elements of biological extraction data to a taste index. Training data may be obtained from previous iterations of machine-learning processes, user inputs, and/or expert inputs. For example, genetic disorder training data 128 correlates biological indices of genetic disorder and genetic markers to genetic disorder labels. As used in this disclosure, a "genetic marker" is a DNA sequence with a known physical location on a chromosome. Genetic markers may link a genetic disorder with a responsible gene. Examples of genetic markers include but are not limited to Restriction fragment length polymorphism (RFLP), single nucleotide polymorphism (SNP), restriction site associated DNA markers (RAD markers), and the like. For example, an SNP is the substitution of a C for a G in the nucleotide sequence AACGAT, thereby producing the sequence AACCAT. SNPs may act as chromosomal tags to specific regions of DNA, and these regions can be scanned for variations that may be involved in a genetic disorder. Such SNPs associated with a genetic disorder may be used as diagnostic tool. Additionally, "genetic disorder labels," as used in this disclosure, are genetic disorders that may be used to tag a genetic disorder. For example in children, fetal hemoglobin (HbF) at 10% concentration and α-thalassemia are the two well-studied biomarkers in sickle cell anemia. An SNP may identify a single nucleotide difference in a healthy phenotype of a DNA sequence of the hemoglobin HBB gene (G-A-G) in contrast to an affected phenotype at the same location (G-T-G). For example, the presence of HbF and α-thalassemia in addition to the presence of the abnormal phenotype may be tagged with "Sickle Cell Anemia." Computing device 104 may train genetic disorder classifier 124 using genetic disorder training data 128.

Still with reference to FIG. 1, computing device 104 may classify, using genetic disorder classifier 124, at least one biological index and at least one genetic marker to a positive result for a genetic disorder. A "positive result" for a genetic disorder, as defined by this disclosure, is a test result where at least one biological indicator for a genetic disorder may be found. A positive result may indicate that the user may be presently suffering from a genetic disorder. Alternatively, a positive result may also indicate that the user may develop a genetic disorder in the future. For example, a positive test for breast cancer may indicate that biological indices BRCA1 and BRCA2 are present. A positive result may be obtained based a population screening test conducted to identify asymptomatic individuals from within a particular community or a subsection of that community who have an increased chance of having a specific genetic disorder, of carrying a specific genetic predisposition to disease or of being a carrier of a recessive genetic variant. A description on machine learning and the use of classifiers follows below.

Figure 3:
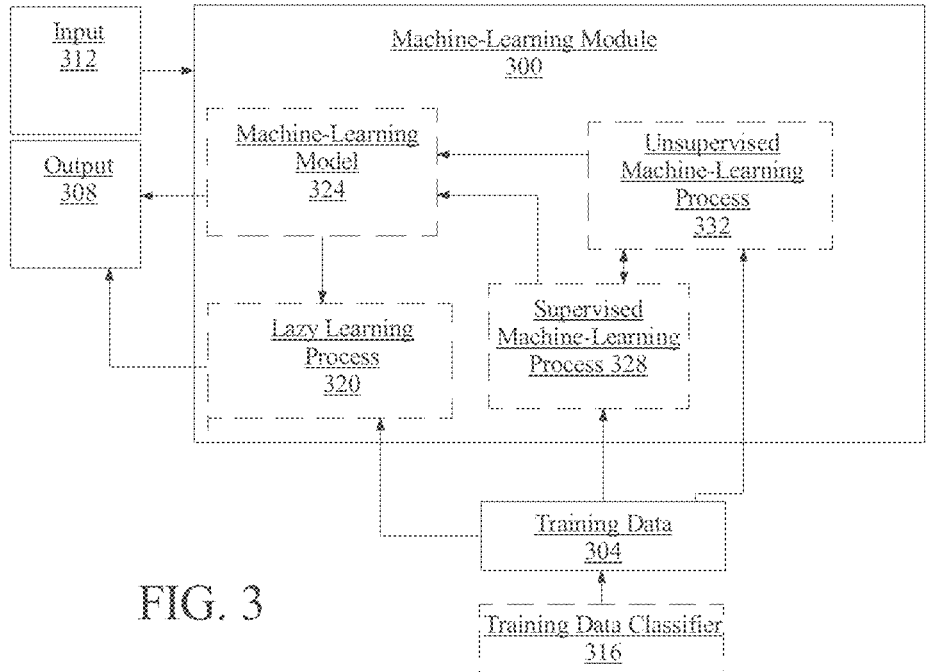
FIG. 3 is a block diagram of an exemplary embodiment of a machine-learning module.

Referring now to FIG. 3, an exemplary embodiment of a machine-learning module 300 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 304 to generate an algorithm that will be performed by a computing device/module to produce outputs 308 given data provided as inputs 312; this contrasts with a non-machine learning software program where the commands to be executed are determined in advance by a user and written in a programming language.

Still referring to FIG. 3, "training data," as used herein, is data containing correlations that a machine-learning process may use to model relationships between two or more categories of data elements. For instance, and without limitation, training data 304 may include a plurality of data entries, each entry representing a set of data elements that were recorded, received, and/or generated together; data elements may be correlated by shared existence in each data entry, by proximity in a given data entry, or the like. Multiple data entries in training data 304 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 304 according to various correlations; correlations may indicate causative and/or predictive links between categories of data elements, which may be modeled as relationships such as mathematical relationships by machine-learning processes as described in further detail below. Training data 304 may be formatted and/or organized by categories of data elements, for instance by associating data elements with one or more descriptors corresponding to categories of data elements. As a non-limiting example, training data 304 may include data entered in standardized forms by persons or processes, such that entry of a given data element in a given field in a form may be mapped to one or more descriptors of categories. Elements in training data 304 may be linked to descriptors of categories by tags, tokens, or other data elements; for instance, and without limitation, training data 304 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 3, training data 304 may include one or more elements that are not categorized; that is, training data 304 may not be formatted or contain descriptors for some elements of data. Machine-learning algorithms and/or other processes may sort training data 304 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category because of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 304 to be made applicable for two or more distinct machine-learning algorithms as described in further detail below. Training data 304 used by machine-learning module 300 may correlate any input data as described in this disclosure to any output data as described in this disclosure. As a non-limiting illustrative example, genetic disorder biological indices may serve as inputs, outputting other potential health disorders that a may use the same and/or related biological indices.

Further referring to FIG. 3, training data may be filtered, sorted, and/or selected using one or more supervised and/or unsupervised machine-learning processes and/or models as described in further detail below; such models may include without limitation a training data classifier 316. Training data classifier 316 may include a "classifier," which as used in this disclosure is a machine-learning model as defined below, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 300 may generate a classifier using a classification algorithm, defined as a process whereby a computing device and/or any module and/or component operating thereon derives a classifier from training data 304. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 316 may classify elements of training data to classify a genetic disorder into categories such as a single gene disorders, complex gene disorders, chromosomal disorders, and the like.

Still referring to FIG. 3, machine-learning module 300 may be configured to perform a lazy-learning process 320 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 304. Heuristic may include selecting some number of highest-ranking associations and/or training data 304 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 3, machine-learning processes as described in this disclosure may be used to generate machine-learning models 324. A "machine-learning model," as used in this disclosure, is a mathematical and/or algorithmic representation of a relationship between inputs and outputs, as generated using any machine-learning process including without limitation any process as described above and stored in memory; an input is submitted to a machine-learning model 324 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 324 may be generated by creating an artificial neural network, such as a convolutional neural network comprising an input layer of nodes, one or more intermediate layers, and an output layer of nodes. Connections between nodes may be created via the process of "training" the network, in which elements from a training data 304 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 3, machine-learning algorithms may include at least a supervised machine-learning process 328. At least a supervised machine-learning process 328, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include a biological index such as interleukin (IL)-6 as described above as inputs, with at least rheumatoid arthritis as an output of a genetic disorder, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 304. Persons skilled in the art, upon reviewing the entirety of this disclosure, will be aware of various possible variations of at least a supervised machine-learning process 328 that may be used to determine relation between inputs and outputs. Supervised machine-learning processes may include classification algorithms as defined above.

Further referring to FIG. 3, machine learning processes may include at least an unsupervised machine-learning processes 332. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 3, machine-learning module 300 may be designed and configured to create a machine-learning model 324 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 3, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Referring back to FIG. 1, in an embodiment, computing device 104 may receive disease training data and train a machine-learning model using the disease training data. The disease training data correlates biological indices of genetic disorders with related disease states. As used in this disclosure, a "related disease state" refers to a disease state that may share a biological index with another disease state or may indicate a predisposition for another disease state. As a non-limiting example, a lymphoblastoid expression of the proteins ORMDL3 and GSDML may show an association with asthma. Another non-limiting example may include a variant of MAPT that is associated with progressive supranuclear palsy which is also associated with MAPT mRNA expression. Computing device 104 may output a plurality of related disease states based on the machine-learning model. One of ordinary skill would understand after reviewing the entire content of this disclosure other possible associations between a biological index and a related disease state. By employing optimization methods involving machine-learning models to generate the associations between a biological index and a related disease state, such analysis may show a person's predisposition to another category of disease such as cardiovascular disease, cancer, pulmonary disease, neurological disease, endocrine disease, viral outbreaks, digestive disease, psychiatric disease, autoimmune disease, bacterial infections, blood diseases, congenital diseases, connective tissue disease, ears/nose/throat diseases, eye diseases, reproductive diseases, immune system diseases, urinary diseases, metabolic disorders, musculoskeletal diseases, parasitic diseases, skin diseases, body degradation, body inflammation, and the like.

With continued reference to FIG. 1, computing device 104 may generate sustenance plan 132 as a function of the positive result. As defined in this disclosure, a "sustenance plan" is an instruction set for consumption of a plurality of sustenance compositions which, as used in this disclosure, may help relieve and/or slow the progression of, for example, a genetic disorder. "Sustenance compositions," as used in this disclosure, may include any combination of ingredients that may be treated as a meal or a snack or any beverages or combination of beverages that may be consumed by a user. Sustenance plan 132 may include, for example, what type of sustenance compositions a user may want to consume based on the desire to relieve and/or prevent a genetic disorder. Sustenance plan 132 may include what specific time of the day the user should consume the sustenance compositions. Sustenance plan 132 may include a list of sustenance compositions to avoid based on a genetic disorder. Sustenance plan 132 may include a list of acceptable sustenance compositions substitutes in case a sustenance composition suggested to the user is not available. Sustenance plan 132 may include a list of nutritional supplements that may relieve and/or prevent one or more genetic disorders. Sustenance plan 132 may include information as to how to safely take the supplements as well as information regarding any potential adverse effects.

Additionally or alternatively, with reference to FIG. 1, computing device 104 may be configured to generate the sustenance plan based on the plurality of related disease states and the genetic disorder. For instance, Phenylketonuria (PKU) is a type of amino acid metabolism disorder preventing the metabolism of phenylalanine (Phe). A low-protein diet may help manage Phenylketonuria. Similarly, a low-protein diet may help manage a disease state related to phenylketonuria which may affects the kidneys. Examples of a low protein sustenance plan may include the consumption of fruits such as bananas and any type of berries; vegetables such as leafy green vegetables, peppers, broccoli, and the like; and grains such as rice, oats, barley, and the like.

Referring still to FIG. 1, computing device 104 may be configured to receive a second input. The second input may include any of the inputs as described for input 112. For example, a second input may correspond to a second sample taken after commencing use of sustenance plan 132. A medical professional may want to retest a user to check for changes in the presence or absence of biological index 120. Computing device 104 may reclassify at least one biological index and the at least one genetic marker from the second input to a positive result of the genetic disorder. Computing device 104 may update the alimentary plan as a function of the second input. As a non-limiting example, SNPs related to obesity, such as FTO and MC4R may still be present in a genetic test. Sustenance plan 132 generated to address a person's weight, may contain but not limited to an increase in the consumption of fruits and vegetables and a reduction in the caloric intake suggested by a decrease in the meal size. Sustenance plan 132 may be updated to, for example, further reduce the caloric intake and increase the consumption of fiber.

Figure 4:
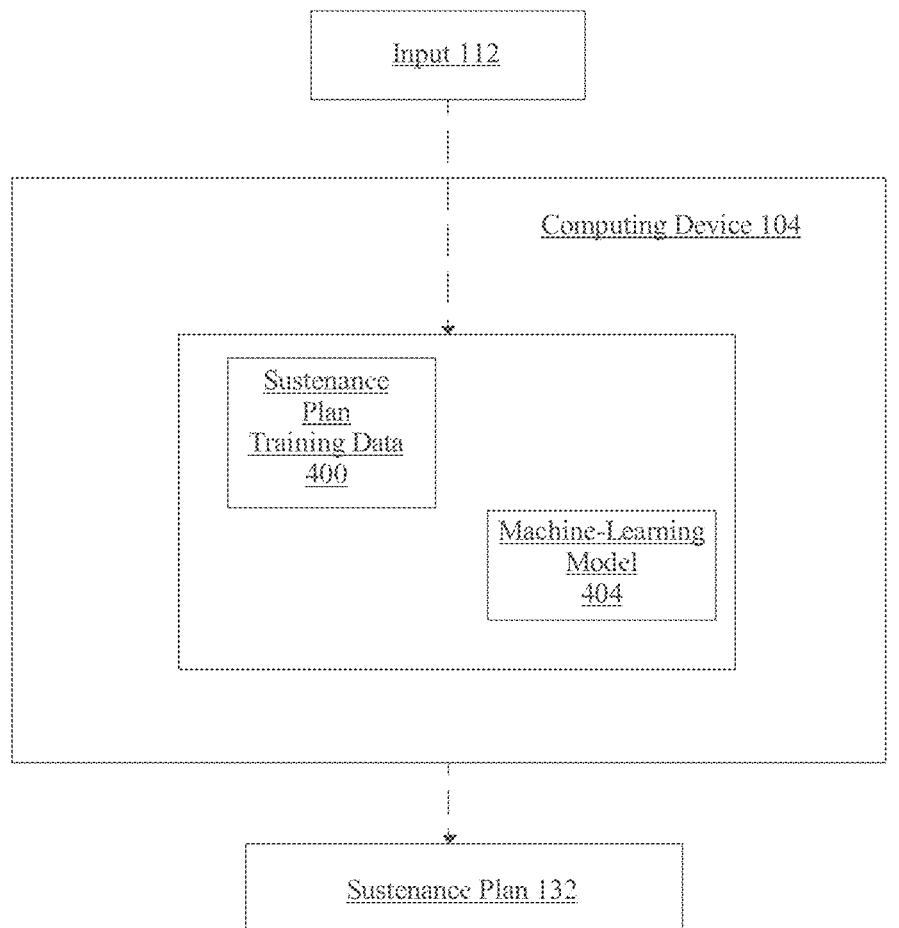
FIG. 4 is a block diagram of an exemplary embodiment of a determination of a sustenance plan as a function of a machine-learning process.

Now referring to FIG. 4, an exemplary embodiment of the generation of sustenance plan 132 implementing a machine learning model is described. Computing device 104 is configured to receive input 112. Computing device 104 may receive sustenance plan training data 400. Sustenance plan training data 400 may be received and/or collected by experts or collected from users that may have received and used an alimentary plan. Sustenance plan training data 400 may be received as a function of user-entered valuations of sustenance plans, sustenance plan metrics, and/or measurable values. The vector training set may be received by one or more past iterations of the previous sustenance plan vectors. The vector training set may be received by one or more remote devices that at least correlate a sustenance plan element and genetic disorder metric to a measurable value, wherein a remote device is an external device to computing device 104. A machine-learning model 404 is trained using sustenance plan training data 400. Sustenance plan training data 400 correlates sustenance plans with a historical ameliorative effect on a genetic disorder. For example, sustenance training data 400 would include those sustenance plans that have relieved symptoms and/or effects of a genetic disorder. Sustenance plan 132 is outputted as a function of the machine-learning model. The machine-learning model may be implemented, without any limitations, as described earlier in this disclosure. In another embodiment, generating sustenance plan 132 may include outputting a message independent of the presence of the plurality of alimentary plans. For example, sustenance plan training data 400 may not contain values for a particular genetic disorder. As a result, sustenance plan 132 may not be a suitable sustenance plan to treat and/or prevent and/or improve the particular genetic disorder. As such, a message may be outputted indicating this disorder. The message may be outputted directly to a user device, a web page, an email message, and the like. An example of a message may include, "No nutrition suggestions are available for this genetic disorder."

Figure 5:
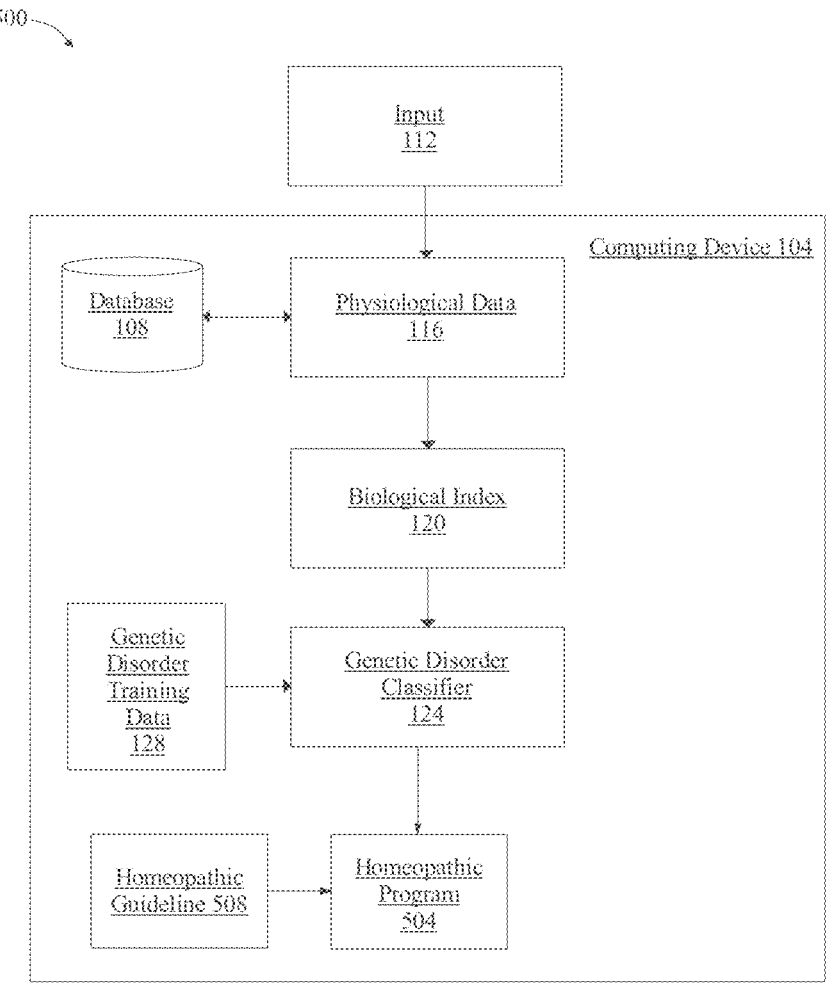
FIG. 5 is a block diagram of an exemplary embodiment of a system for generating a homeopathic program for managing a genetic disorder.

Now referring to FIG. 5, an exemplary embodiment of a system 500 for producing a homeopathic guideline for managing genetic disorders is illustrated. System 500 includes computing device 104. Computing device 104 may include any computing device 104 as described above in detail, in reference to FIG. 1. For example and without limitation, computing device 104 may include a microcontroller, microprocessor, digital signal processor (DSP) and/or system on a chip (SoC) as described in this disclosure. Computing device 104 is configured to receive at least one genetic marker and an input 112 comprising genetics test data. Genetic marker includes any of the genetic marker as described above in reference to FIGS. 1-4. Input 112 includes any of the input 112 as described above, in reference to FIGS. 1-4. Computing device 104 is configured to identify a plurality of biological indices of a disease state as a function of the genetics test data, wherein the plurality of biological indices comprises at least one biological index 120 related to a genetic disease state. Biological index 120 includes any of the biological index 120 as described above, in reference to FIGS. 1-4. Computing device 104 is configured to generate a genetic disorder classifier 124. Genetic disorder classifier 124 includes any of the genetic disorder classifier 124 as described above, in reference to FIGS. 1-4. Computing device 104 generates genetic disorder classifier 124 as a function of receiving genetic disorder training data 128 correlating biological indices of genetic disorders and genetic markers to genetic disorder labels and training genetic disorder classifier 124 using genetic training data 128. Genetic disorder training data 128 includes any of the genetic disorder training data 128 as described above, in reference to FIGS. 1-4. Computing device 104 is configured to input the at least one biological index and the at least one genetic marker into the genetic disorder classifier and classify, using the genetic disorder classifier, the at least one biological index and the at least one genetic marker to a genetic disorder, as described above in reference to FIGS. 1-4.

In an embodiment, and still referring to FIG. 5, classifying the at least one biological index and the at least one genetic marker to a genetic disorder may further comprise receiving a predisposition index. As used in this disclosure a "predisposition index" is a biological entity found in any body fluid, for example blood, skin sample, or the like, that indicates a likelihood and/or predisposition of a disorder or a disease. In an embodiment, and without limitation, a predisposition index may be classified as a predisposition biological index. As used in this disclosure a "predisposition biological index" is a biological indicator used to predict what group of patients have a high propensity for developing a genetic disorder. For example, and without limitation, predisposition index may include one or more biological indicators comprising E3 ubiquitin protein ligase, 15q11, 15q12, 15q13, and the like thereof. In another embodiment, and without limitation, predisposition index may be classified as a predictive biological index, wherein a predictive biological index is a biological indicator used to predict what group of patients will respond favorably or unfavorably to a particular treatment as described above, in reference to FIGS. 1-4.

Still referring to FIG. 5, computing device 104 is configured to produce a homeopathic program 504 as function of the genetic disorder. As used in this disclosure a "homeopathic program" is a program and/or instruction set to alter an individual's genes and/or genetic disorder. A homeopathic program may provide instruction relating to one or more areas of a user's life, including but not limited to, physical fitness, stress management, meditation, spirituality, religion, energy healing, professional endeavors, personal endeavors, body, mind, health, finances, recreation, romance, personal development, and the like. For example, and without limitation, homeopathic program 504 may include a program that instructs an individual to perform 10 minutes of strenuous exercise every day for 5 weeks. As a further non-limiting example, homeopathic program 504 may include a program that instructs an individual to meditate for 1 minute every other week. As a further non-limiting example, homeopathic program 504 may instruct an individual to go on a hike for 2 hours once a week. Additionally or alternatively, homeopathic program 504 may include a sustenance plan 132, wherein sustenance plan 132 is described above in detail, in reference to FIGS. 1-4. For example, and without limitation, homeopathic program 504 may instruct an individual to consume a paleo diet. In an embodiment and without limitation, homeopathic program 504 may include one or more instructions such as, but not limited to a first instruction to exercise and a second instruction of a nourishment program.

Still referring to FIG. 5, computing device 104 identifies homeopathic program as a function of receiving a homeopathic guideline 508. As used in this disclosure a "homeopathic guideline" is a recommendation and/or guideline associated to an individual's genetic system. For example, and without limitation, homeopathic guideline 508 may denote that an individual's genetic system may comprise 10-15 kbp. As a further non-limiting example, homeopathic guideline 508 may denote that an individual's genetic system may comprise 0.2 kb of a tyrosine tRNA gene. As a further non-limiting example, homeopathic guideline 508 may denote that an individual's genetic system may comprise 2500 kb of a dystrophin gene. In an embodiment, and without limitation, receiving homeopathic guideline 508 may further comprise obtaining a homeopathic input. As used in this disclosure a "homeopathic input" is an input received from one or more informed advisors. For example, and without limitation, homeopathic input may be received as a function of one or more homeopathic databases. As used in this disclosure a "homeopathic database" is a database containing one or more homeopathic guidelines. Homeopathic database may be implemented, without limitation, as a relational databank, a key-value retrieval databank such as a NOSQL databank, or any other format or structure for use as a databank that a person skilled in the art would recognize as suitable upon review of the entirety of this disclosure. Homeopathic database may alternatively or additionally be implemented using a distributed data storage protocol and/or data structure, such as a distributed hash table or the like. Homeopathic database may include a plurality of data entries and/or records as described above. Data entries in a databank may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a databank may store, retrieve, organize, and/or reflect data and/or records as used herein, as well as categories and/or populations of data consistently with this disclosure. Homeopathic database may include a peer review. Peer review may identify one or more expected responses as a function of a peer review evaluation conducted by one or more informed advisors with similar competencies. As a non-limiting example peer review may include professional peer reviews, scholarly peer reviews, government peer reviews, medical peer reviews, technical peer reviews, and the like thereof. As a non-limiting example peer review may include professional peer reviews, scholarly peer reviews, government peer reviews, medical peer reviews, technical peer reviews, and the like thereof. Homeopathic database may include an informed advisor association. Informed advisor association may identify one or more expected responses as a function of one or more committees, organizations, and/or groups. As a non-limiting example informed advisor association may include the such as the American Medical Association, American Psychiatric Association, American Red Cross, Anxiety and Depression Association of America, American Academy of Experts in Traumatic Stress, American Psychological Association, American Academy of Child and Adolescent Psychiatry, and the like thereof. Homeopathic database may include a medical website. Medical website may identify one or more expected responses as a function of one or more online and/or web-based medical recommendations. As a non-limiting example medical website may include Medline Plus, Drugs.com, Mayo Clinic, Orphanet, Medgadget, WebMD, Health.gov, SPM ePatients blog, and the like thereof.

Still referring to FIG. 5, homeopathic guideline may be received as a function of one or more informed advisors, wherein an informed advisor, wherein an informed advisor is an individual capable of recommending and/or guiding an individual towards a more suited wellness state. For example, and without limitation, informed advisor may include one or more nutritionists, personal trainers, physical therapists, spiritual leaders, religious leaders, massage therapists, spiritual therapists, reiki masters, acupuncturists, life coaches, priests, philosophers, theologists, yoga instructors, wellness instructors, teachers, and the like thereof. In an embodiment, salubrious reference may include recommendations from one or more medical sources such as peer reviews, informed advisor associations, medical websites, medical textbooks, religious books, prophecies, spiritual texts, and the like thereof.

Still referring to FIG. 5, computing device 104 identifies homeopathic program 504 as a function of homeopathic guideline 508 and the genetic disorder. In an embodiment, and without limitation, homeopathic program 504 may be identified as a function of homeopathic guideline 508 and the genetic disorder using a homeopathic machine-learning model. As used in this disclosure a "homeopathic machine-learning model" is a machine-learning model that produces a homeopathic program output given homeopathic guidelines and/or genetic disorders as inputs; this is in contrast to a non-machine learning software program where the commands to be executed are determined in advance by a user and written in a programming language. Homeopathic machine-learning model may include one or more machine-learning processes such as supervised, unsupervised, or reinforcement machine-learning processes that computing device 104 and/or a remote device may or may not use in the determination of homeopathic program 504, wherein a remote device is an external device to computing device 104 as described above in detail. A homeopathic machine-learning process may include, without limitation machine-learning processes such as simple linear regression, multiple linear regression, polynomial regression, support vector regression, ridge regression, lasso regression, elasticnet regression, decision tree regression, random forest regression, logistic regression, logistic classification, K-nearest neighbors, support vector machines, kernel support vector machines, naïve bayes, decision tree classification, random forest classification, K-means clustering, hierarchical clustering, dimensionality reduction, principal component analysis, linear discriminant analysis, kernel principal component analysis, Q-learning, State Action Reward State Action (SARSA), Deep-Q network, Markov decision processes, Deep Deterministic Policy Gradient (DDPG), or the like thereof.

Still referring to FIG. 5, computing device 104 may train homeopathic machine-learning process as a function of a homeopathic training set. As used in this disclosure a "homeopathic training set" is a training set that correlates a homeopathic guideline and/or genetic disorder to a homeopathic program. For example, and without limitation, a homeopathic guideline of 11 kbp and a genetic disorder of short telomere syndromes may relate to a homeopathic program of exercise for 30 minutes and increased meditation to reduce inflammation. The homeopathic training set may be received as a function of user-entered valuations of homeopathic guidelines, genetic disorders, and/or homeopathic programs. Computing device 104 may receive homeopathic training set by receiving correlations of homeopathic guidelines and/or genetic disorders that were previously received and/or determined during a previous iteration of determining homeopathic programs. The homeopathic training set may be received by one or more remote devices that at least correlate a homeopathic guideline and/or genetic disorder to a homeopathic program, wherein a remote device is an external device to computing device 104, as described above. Homeopathic training set may be received in the form of one or more user-entered correlations of a homeopathic guideline and/or genetic disorder to a homeopathic program. Additionally or alternatively, a user may include, without limitation, an informed advisor and/or a functional advisor entering correlations of homeopathic guidelines and/or genetic disorders to homeopathic programs, wherein informed advisors and/or functional advisors may include, without limitation, physicians, nutritionists, therapists, spiritual leaders, and the like thereof as described above in detail.

Still referring to FIG. 5, computing device 104 may receive homeopathic machine-learning model from a remote device that utilizes one or more homeopathic machine learning processes, wherein remote device is described above in detail. For example, and without limitation, remote device may include a computing device, external device, processor, and the like thereof. Remote device may perform the homeopathic machine-learning process using the homeopathic training set to generate homeopathic program 504 and transmit the output to computing device 104. Remote device may transmit a signal, bit, datum, or parameter to computing device 104 that at least relates to homeopathic program 504. Additionally or alternatively, the remote device may provide an updated machine-learning model. For example, and without limitation, an updated machine-learning model may be comprised of a firmware update, a software update, a homeopathic machine-learning process correction, and the like thereof. As a non-limiting example a software update may incorporate a new homeopathic guidelines that relates to a modified genetic disorder. Additionally or alternatively, the updated machine learning model may be transmitted to the remote device, wherein the remote device may replace the homeopathic machine-learning model with the updated machine-learning model and determine the homeopathic program as a function of the homeopathic guideline using the updated machine-learning model. The updated machine-learning model may be transmitted by the remote device and received by computing device 104 as a software update, firmware update, or corrected homeopathic machine-learning model. For example, and without limitation a homeopathic machine-learning model may utilize a neural net machine-learning process, wherein the updated machine-learning model may incorporate polynomial regression machine-learning process. Updated machine learning model may additionally or alternatively include any machine-learning model used as an updated machine learning model as described in U.S. Nonprovisional application Ser. No. 17/106,658, the entirety of which is incorporated herein by reference. In an embodiment, and without limitation, homeopathic machine-learning model may identify homeopathic program 504 as a function of one or more classifiers, wherein a classifier is described above in detail.

Still referring to FIG. 5, homeopathic program 504 may include a mitigation goal. As used in this disclosure a "mitigation goal" is a goal that is designed to reduce the symptoms and/or effects of a genetic disorder. For example, and without limitation, mitigation goal may include reducing the effects of albinism as a function of recommending magnesium and/or zinc supplements and/or recommending enhanced chakra flow of an individual's body. As a further non-limiting example, mitigation goal may include one or more actions to affect a cytokine expression, inflammatory process, anti-oxidative response and/or protease degradation. In an embodiment, and without limitation, homeopathic program 504 may include a treatment goal. As used in this disclosure a "treatment goal" is a goal that is designed to at least reverse and/or eliminate genetic disorder. As a non-limiting example, a treatment goal may include reversing the effects of down syndrome as a function of exercise, diet, and/or supplementation. As a further non-limiting example, a treatment goal includes reversing congenital adrenal hyperplasia as a function of recommending the supplement N-acetyl cysteine, recommending edibles such as apples, berries, tomatoes, celery, onions, sauerkraut, kombucha, and the like thereof, recommending a meditation schedule of once per day for 20 minutes, and/or recommending 25 minutes of exercise every other day. Homeopathic program 504 may include a prevention goal. As used in this disclosure a "prevention goal" is a goal that is designed to at least prevent and/or avert genetic disorder. As a non-limiting example, a prevention goal may include preventing the development of the asthma as a function of hiking 2 miles per day and/or recommending a nourishment program of a low-carb diet. Disorder functional goal may include a mitigation goal.

Still referring to FIG. 5, homeopathic program 504 may include an epigenetic goal. As used in this disclosure an "epigenetic goal" is a goal that is designed to modify and/or alter one or more genes and/or gene expressions of an individual. For example, and without limitation, epigenetic goal may include one or more goals to methylate DNA where a cytosine residue that is followed by a guanine residue may be methylated. As a further non-limiting example, epigenetic goal may include one or more goals to alter one or more histone groups such as but not limited to acetylation of histone tails, chemical modifications, and the like thereof. As a further non-limiting example, epigenetic goal may include a goal to modify one or more structures comprising RNA, microRNA, noncoding sequences, and the like thereof. Additionally or alternatively, homeopathic program 504 may include a targeted gene therapy. As used in this disclosure a "targeted gene therapy" is a therapy designed and/or configured to alter a gene expression of a specific gene of a genomic sequence. For example, and without limitation, targeted gene therapy may be designed to block and/or turn off signals that encourage cell proliferation. As a further non-limiting example, targeted gene therapy may be designed to prevent cells from exceeding a cell lifecycle. As a further non-limiting example, targeted gene therapy may be designed to induce apoptosis and/or necrosis of a cell.

In an embodiment, and still referring to FIG. 5, producing homeopathic program 504 may further comprise determining a genetic locus. As used in this disclosure a "genetic locus" is a fixed position on a chromosome that houses and/or contains a particular gene and/or genetic marker. In an embodiment, and without limitation, genetic locus may include one or more locations and/or positions on a chromosome, wherein a chromosome may comprise a plurality of genetic locations and/or protein coding genes. In another embodiment, and without limitation, genetic locus may include one or more cytogenetic bands and/or packaged DNA, wherein a cytogenetic band may include, but is not limited to, a p arm and/or a q arm. In an embodiment, and without limitation, genetic locus may be located in a chromosome region and/or a sub-band. For example, a genetic locus may 3p22.1, wherein the gene may be housed on chromosome 3, in the p arm, in region and/or band 2, and in sub-band 1. In an embodiment, and without limitation, computing device 104 may produce homeopathic program 504 as a function of the genetic locus. For example, and without limitation, computing device may receive from a genetic database one or more homeopathic treatments that are designed and/or configured to treat and/or affect genetic locus. In another embodiment, and without limitation, computing device 104 may perform one or more machine-learning processes to identify one or more homeopathic programs designed and/or configured to target and/or affect genetic locus.

In an embodiment, and still referring to FIG. 5, computing device 104 may identify homeopathic program 504 as a function of receiving a conduct indicator. As used in this disclosure a "conduct indicator" is an element of data denoting an individual's lifestyle choices. In an embodiment conduct indicator may include one or more biological, psychological, social, and/or spiritual elements. For example, and without limitation, conduct indicator may denote a biological element, wherein the biological indicator may denote that an individual has low cholesterol and/or exercises frequently. As a further non-limiting example, conduct indicator may denote a psychological element, wherein the psychological element may denote that an individual is happy and/or content. As a further non-limiting example, conduct indicator may denote a social element, wherein the social element may indicate that an individual has 36 friends. As a further non-limiting example, conduct indicator may denote a spiritual element, wherein the spiritual element may indicate that an individual belongs to the Hinduism religion. As a further non-limiting example, spiritual element may denote one or more chakras and/or spiritual energies of an individual. In an embodiment conduct indicator may denote one or more lifestyles groups such as, but not limited to, general lifestyles, income, profession, and/or occupation lifestyles, consumption-based lifestyles, social and/or political lifestyles, marketing lifestyles, military lifestyles, sexual lifestyles, spiritual lifestyles, religious lifestyles, musical lifestyles, recreational lifestyles, and the like thereof. For example, and without limitation, lifestyles may include activism, asceticism, modern primitivism, bohemianism, communal living, clothes free, groupie lifestyle, hippie, quirkyalone, rural lifestyle, simple living, traditional lifestyle, criminality, farming, jet set, piracy, poverty, prostitution, sarariman, workaholic, yuppie, social liberalism, social conservatism, polygamy, monogamy, ahimsa, Hinduism, Christianity, evangelicalism, Islam, Judaism, missionary, Zen, yoga, Thelema, surfer, athleticism, hunter, artist, golf, recreational drug use, and the like thereof. Additionally or alternatively conduct indicator may include one or more markers associated with an individual's behavior such as, but not limited to, markers associated to genetics test data. For example, and without limitation markers may include but are not limited to biological samples, biomarkers, genetic test data, and the like thereof as defined above, in reference to FIG. 1.

Still referring to FIG. 5, conduct indicator may include a dimensional element. As used in this disclosure a "dimensional element" is an element of datum denoting a relative measure of wellness of an individual. For example, and without limitation dimensional element may denote one or more dimensions associated with healthy living. In an embodiment dimensional element may include an occupational dimension. As used in this disclosure an "occupational dimension" is a dimension of wellness representing personal satisfaction and enrichment in an individual's life through work and/or occupation. For example, and without limitation, occupational dimension may denote that an individual's job is rewarding due to the contribution of personal values, interests, and/or beliefs that are shared among the job and the individual. In an embodiment dimensional element may include a physical dimension. As used in this disclosure a "physical dimension" is a dimension of wellness representing physical activity and/or nutrition. For example, and without limitation, physical dimension may include a dimension associated with eating whole grain foods and/or lean protein foods diet and/or nutrition, while concurrently discouraging the use of recreational drugs. As a further non-limiting example, physical dimension may include a dimension associated with regular exercise and/or enhanced physical strength. In an embodiment dimensional element may include a social dimension. As used in this disclosure a "social dimension" is a dimension of wellness representing an individual's contributions towards the environment and/or community. For example, and without limitation, social dimension may include a dimension associated with an individual's contributions towards the common welfare of the community and/or living in harmony with other.

In an embodiment and still referring to FIG. 5, dimensional element may include an intellectual dimension. As used in this disclosure a "intellectual dimension" is a dimension of wellness representing an individual's creative and/or mental activities. For example, and without limitation, intellectual dimension may include a dimension associated with an individual's abilities to identify potential problems and choose appropriate courses of action based on available information than to wait, worry, and contend with major concerns later. In an embodiment dimensional element may include a spiritual dimension. As used in this disclosure a "spiritual dimension" is a dimension of wellness representing an individual's search for meaning and/or purpose of existence. For example, and without limitation, spiritual dimension may include a dimension associated with an individual's understanding of the meaning for existence and/or the tolerance of other's meaning for existence. In an embodiment dimensional element may include an emotional dimension. As used in this disclosure an "emotional dimension" is a dimension of wellness representing an individual's awareness and/or acceptance of feelings. For example, and without limitation, emotional dimension may include a dimension associated with an individual's feelings related to a belief, philosophy, behavior, and the like thereof.

Still referring to FIG. 5, computing device 104 may conduct indicator include an exposure element. As used in this disclosure an "exposure element" is an element of datum representing contact and/or exposure associated with a lifestyle. For example, and without limitation exposure element may denote prolonged contact to radioactive material as a function of being a nuclear power plant technician. As a further non-limiting example exposure element may denote prolonged contact to illicit drugs as a function of being a recreational drug user. As a further non-limiting example, exposure element may denote prolonged contact to heavy metals in water as a function of having a surfing lifestyle. In an embodiment, and without limitation, exposure element may denote one or more exposures to toxins such as, but not limited to, persistent organic pollutants, polychlorinated bisphenols, hydrogen chlorides, benzenes, xylenes, toluenes, dioxins, heavy metals, radioactivity, and the like thereof. In another embodiment, exposure element may denote one or more epigenetic factors. As used in this disclosure an "epigenetic factor" is a factor denoting a likelihood of a change in gene activity and/or expression as a function of one or more external factors. For example, and without limitation, epigenetic factor may denote a high likelihood for a gene mutation as a function of a polyaromatic hydrocarbon. As a further non-limiting example, epigenetic factor may denote a high likelihood for reduced gene expression as a function of aluminum toxicity and/or poisoning.

Still referring to FIG. 5, producing homeopathic program 504 may further comprise determining an inheritance element. As used in this disclosure an "inheritance element" is an element of data representing one or more genes and/or gene expressions that are inherited by a parent. In an embodiment, and without limitation, inheritance element may denote that an individual comprises one or more Mendelian and/or monogenetic inheritances. In another embodiment, and without limitation, inheritance element may denote that an individual comprises one or more autosomal dominant inheritances, wherein an autosomal dominant inheritance is an inherited gene in which only one copy of a defective gene is necessary to cause the genetic disorder. In another embodiment, and without limitation, inheritance element may denote that an individual comprises one or more autosomal recessive inheritances, wherein an autosomal recessive inheritance is an inherited gene in which two copies of a defective gene are necessary to cause the condition. In another embodiment, and without limitation, inheritance element may denote that an individual comprises one or more x-linked inheritances, wherein an x-linked inheritance is an inherited gene in which the defective gene is present on the female and/or x-linked chromosome. In another embodiment, and without limitation, inheritance element may denote that an individual comprises one or more multifactorial inheritances, wherein a multifactorial inheritance is an plurality of different inherited genes that aggregate to a common genetic disorder effect. For example, and without limitation, breast cancer susceptibility may be caused as a function of a plurality of genes operating on chromosomes 6, 11, 13, 14, 15, 17, and/or 22.

Still referring to FIG. 5, producing homeopathic program 504 may further comprise determining a root cause. As used in this disclosure a "root cause" is a source of origination of a genetic disorder. For example, and without limitation, root cause may denote that an individual has a sedentary lifestyle as a function of watching television. As a further non-limiting root cause may denote that an individual started smoking as a function of a lack of religious guidance and/or spiritual teaching. As a further non-limiting example, root cause may denote that an individual has emotional instability as a function of one or more traumatic experiences and/or psychological traumas. Additionally or alternatively, producing homeopathic program 504 may further comprise determining a habit. As used in this disclosure a "habit" is a tendency and/or regularly practiced behavior that an individual performs. For example, and without limitation a habit may include swearing, trichotillomania, picking an individual's nose, smoking cigarettes, biting fingernails, drinking coffee, drinking tea, hair picking, watching television, eating fast food, alcohol, emotional shopping, social media use, drinking soda, eating chocolate, humming, sleeping-in, lying, procrastinating, being unfriendly, and the like thereof.

Figure 6:
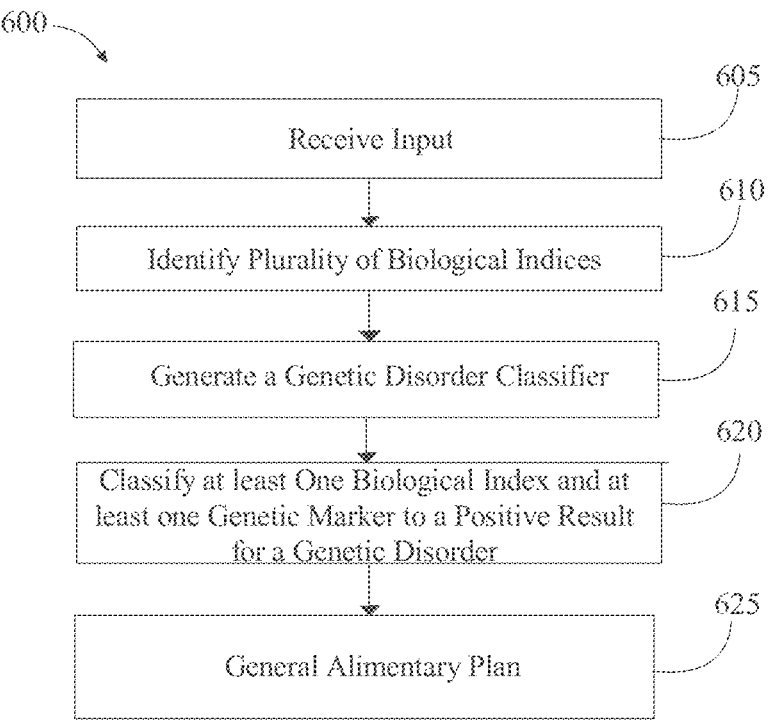
FIG. 6 is a flow diagram illustrating an exemplary embodiment of a method of determining a sustenance plan for managing a genetic disorder.

Referring now to FIG. 6, an exemplary method 600 for generating an alimentary plan to manage a genetic disorder is described. At step 605, a computing device receives an input. The input includes genetics test data, where the genetics test data includes data from a biochemical genetic test. This step may be implemented, without limitation, as described in FIGS. 1-5. The genetics test data may include results of a diagnostic genetic test. The genetics test data may include data from a nutritional assessment. In an embodiment computing device is configured to output an adverse effect on the genetic disorder as a function of the nutritional assessment.

With continued reference to FIG. 6, at step 610, computing device may identify a plurality of biological indices based on the genetics test data. The plurality of biological indices includes at least one biological index based on the genetics test data. This step may be implemented, without limitation, as described in FIGS. 1-5. In an embodiment, computing device may be configured to analyze a progression of the genetic disorder as a function of the at least one biological index.

Still with reference to FIG. 6, at step 615, computing device may generate a genetic disorder classifier. Computing device may generate a genetic disorder classifier by receiving genetic disorder training data correlating biological indices of genetic disorders and genetic markers to genetic disorder labels. Computing device may train genetic disorder classifier using genetic disorder training data. This step may be implemented, without limitation, as described in FIGS. 1-5.

Additionally or alternatively, with continued reference to FIG. 6, computing device may receive disease training data and train a machine-learning model using the disease training data. Computing device may output a plurality of related disease states as a function of the machine-learning model. This may be implemented, without limitations, as described in FIGS. 1-5.

With continued reference to FIG. 6, at step 620, computing device may classify, using genetic disorder classifier at least one biological index and at least one genetic marker to a positive result for a genetic disorder. This step may be implemented, without limitations, as described in FIGS. 1-5.

Still referencing FIG. 6, at step 625, computing device may generate a sustenance plan as a function of the positive result. This step may be implemented, without limitations, as described in FIGS. 1-5. In an embodiment, computing device may be configured to generate a sustenance plan based on the plurality of related disease states and the genetic disorder.

Additionally or alternatively, with continued reference to FIG. 6, in an embodiment, computing device may be configured to receive a second input. Computing device my reclassify at least one biological index and the at least one genetic marker from the second input to a positive result of the genetic disorder. Computing device may update the alimentary plan as a function of the second input. The above may be implemented, without limitation, as described in FIGS. 1-5.

In another embodiment, computing device may receive sustenance plan training data that correlates sustenance plans with a historical ameliorative effect on a genetic disorder. The machine training data may be used to train a machine-learning model. A sustenance plan is outputted as a function of the machine-learning model. In a further embodiment, generating the sustenance plan may include outputting a message independent of the presence of the plurality of alimentary plans. The above may be implemented, without limitation, as described in FIGS. 1-5.

Figure 7:
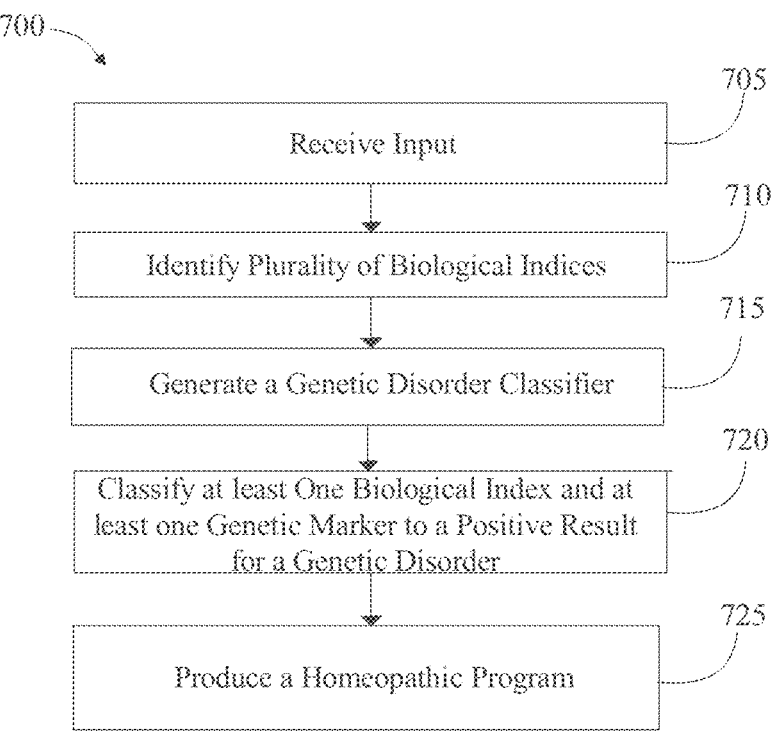
FIG. 7 is a flow diagram illustrating an exemplary embodiment of a method for generating a homeopathic program for managing a genetic disorder.

Now referring to FIG. 7, an exemplary method 700 for generating a homeopathic program to manage a genetic disorder is described. At step 705, a computing device receives an input. The input includes genetics test data, where the genetics test data includes data from a biochemical genetic test. This step may be implemented, without limitation, as described in FIGS. 1-6. The genetics test data may include results of a diagnostic genetic test. The genetics test data may include data from a nutritional assessment. In an embodiment computing device is configured to output an adverse effect on the genetic disorder as a function of the nutritional assessment.

With continued reference to FIG. 7, at step 710, computing device may identify a plurality of biological indices based on the genetics test data. The plurality of biological indices includes at least one biological index based on the genetics test data. This step may be implemented, without limitation, as described in FIGS. 1-6. In an embodiment, computing device may be configured to analyze a progression of the genetic disorder as a function of the at least one biological index.

Still with reference to FIG. 7, at step 715, computing device may generate a genetic disorder classifier. Computing device may generate a genetic disorder classifier by receiving genetic disorder training data correlating biological indices of genetic disorders and genetic markers to genetic disorder labels. Computing device may train genetic disorder classifier using genetic disorder training data. This step may be implemented, without limitation, as described in FIGS. 1-6.

Additionally or alternatively, with continued reference to FIG. 7, computing device may receive disease training data and train a machine-learning model using the disease training data. Computing device may output a plurality of related disease states as a function of the machine-learning model. This may be implemented, without limitations, as described in FIGS. 1-5.

With continued reference to FIG. 7, at step 720, computing device may classify, using genetic disorder classifier at least one biological index and at least one genetic marker to a positive result for a genetic disorder. This step may be implemented, without limitations, as described in FIGS. 1-6.

Still referring to FIG. 7, at step 725, computing device 104 produces a homeopathic program 504. Homeopathic program 504 includes any of the homeopathic program 504 as described above, in reference to FIGS. 1-6. Computing device 104 produces homeopathic program 504 as a function of receiving a homeopathic guideline 508. Homeopathic guideline 508 includes any of the homeopathic guideline 508 as described above, in reference to FIGS. 1-6. Computing device 104 identifies homeopathic program 504 as a function of homeopathic guideline 508 and the genetic disorder.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random-access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 8:
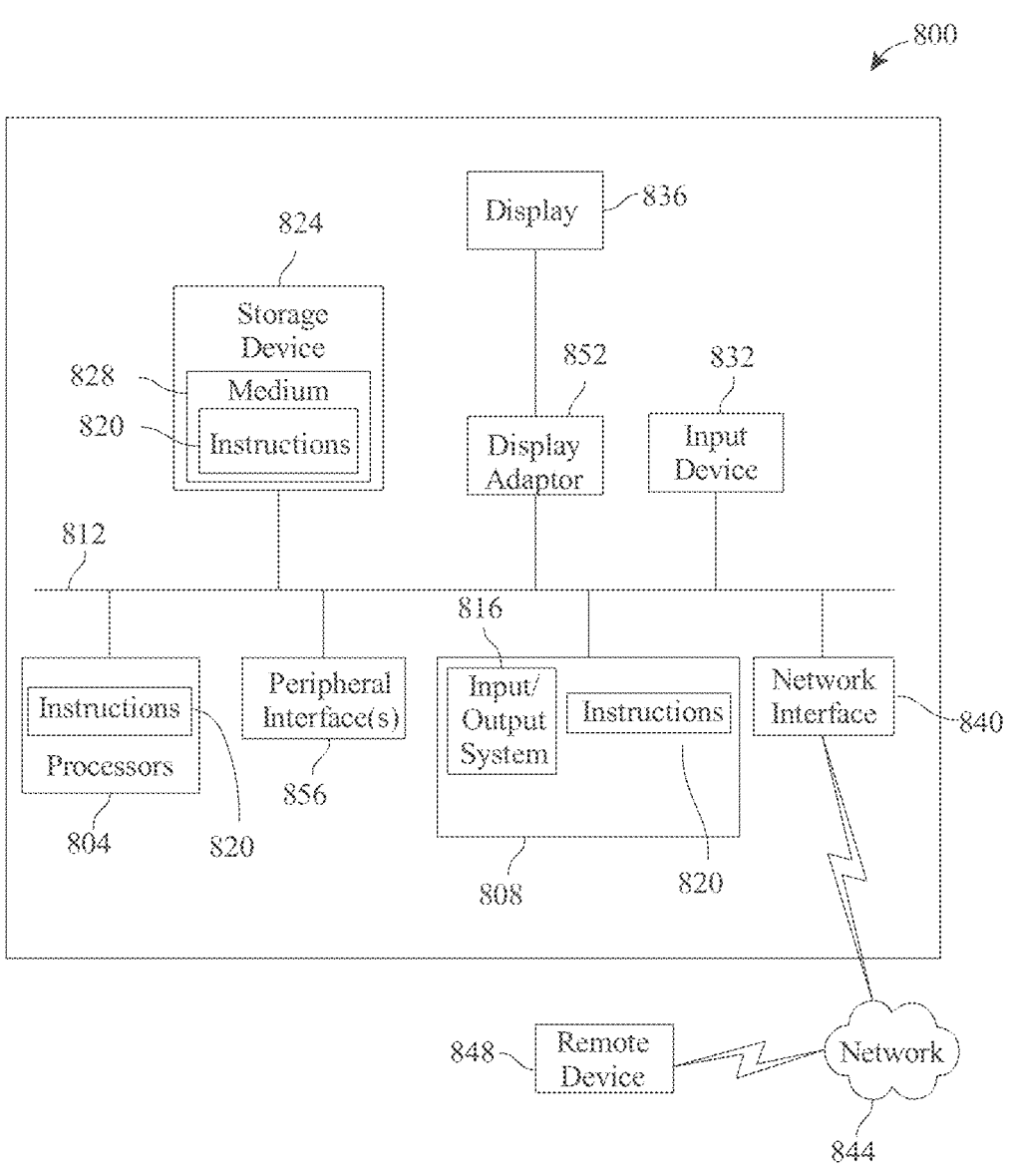
FIG. 8 is a block diagram of a computing system that can be used to implement any one or more of the methodologies disclosed herein and any one or more portions thereof.

FIG. 8 shows a diagrammatic representation of one embodiment of a computing device in the exemplary form of a computer system 800 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 800 includes a processor 804 and a memory 808 that communicate with each other, and with other components, via a bus 812. Bus 812 may include any of several types of bus structures including, but not limited to, a memory bus, a memory controller, a peripheral bus, a local bus, and any combinations thereof, using any of a variety of bus architectures.

Processor 804 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 804 may be organized according to Von Neumann and/or Harvard architecture as a non-limiting example. Processor 604 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating-point unit (FPU), and/or system on a chip (SoC).

Memory 808 may include various components (e.g., machine-readable media) including, but not limited to, a random-access memory component, a read only component, and any combinations thereof. In one example, a basic input/output system 816 (BIOS), including basic routines that help to transfer information between elements within computer system 800, such as during start-up, may be stored in memory 808. Memory 808 may also include (e.g., stored on one or more machine-readable media) instructions (e.g., software) 820 embodying any one or more of the aspects and/or methodologies of the present disclosure. In another example, memory 808 may further include any number of program modules including, but not limited to, an operating system, one or more application programs, other program modules, program data, and any combinations thereof.

Computer system 800 may also include a storage device 824. Examples of a storage device (e.g., storage device 824) include, but are not limited to, a hard disk drive, a magnetic disk drive, an optical disc drive in combination with an optical medium, a solid-state memory device, and any combinations thereof. Storage device 824 may be connected to bus 812 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 824 (or one or more components thereof) may be removably interfaced with computer system 800 (e.g., via an external port connector (not shown)). Particularly, storage device 824 and an associated machine-readable medium 828 may provide nonvolatile and/or volatile storage of machine-readable instructions, data structures, program modules, and/or other data for computer system 800. In one example, software 820 may reside, completely or partially, within machine-readable medium 828. In another example, software 820 may reside, completely or partially, within processor 804.

Computer system 800 may also include an input device 832. In one example, a user of computer system 800 may enter commands and/or other information into computer system 800 via input device 832. Examples of an input device 832 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 832 may be interfaced to bus 812 via any of a variety of interfaces (not shown) including, but not limited to, a serial interface, a parallel interface, a game port, a USB interface, a FIRE-WIRE interface, a direct interface to bus 812, and any combinations thereof. Input device 832 may include a touch screen interface that may be a part of or separate from display 836, discussed further below. Input device 832 may be utilized as a user selection device for selecting one or more graphical representations in a graphical interface as described above.

A user may also input commands and/or other information to computer system 800 via storage device 824 (e.g., a removable disk drive, a flash drive, etc.) and/or network interface device 840. A network interface device, such as network interface device 840, may be utilized for connecting computer system 800 to one or more of a variety of networks, such as network 844, and one or more remote devices 848 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 844, may employ a wired and/or a wireless mode of communication. In general, any network topology may be used. Information (e.g., data, software 820, etc.) may be communicated to and/or from computer system 800 via network interface device 840.

Computer system 800 may further include a video display adapter 852 for communicating a displayable image to a display device, such as display device 836. Examples of a display device include, but are not limited to, a liquid crystal display (LCD), a cathode ray tube (CRT), a plasma display, a light emitting diode (LED) display, and any combinations thereof. Display adapter 852 and display device 836 may be utilized in combination with processor 804 to provide graphical representations of aspects of the present disclosure. In addition to a display device, computer system 800 may include one or more other peripheral output devices including, but not limited to, an audio speaker, a printer, and any combinations thereof. Such peripheral output devices may be connected to bus 812 via a peripheral interface 856. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods and systems to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for producing a homeopathic program for managing genetic disorders, the system comprising:
 a computing device configured to:
  receive at least one genetic marker and an input comprising genetics test data;
  identify a plurality of biological indices of a disease state as a function of the genetics test data, wherein the plurality of biological indices comprises at least one biological index related to a genetic disease state;
  generate a genetic disorder classifier, wherein the generating the genetic disorder classifier comprises:
   receiving genetic disorder training data, wherein the genetic training data correlates biological indices of genetic disorders and genetic markers to genetic disorder labels; and
   training, iteratively, the genetic disorder classifier using the genetic disorder training data, wherein training the genetic disorder classifier includes retraining the genetic disorder classifier with feedback from previous iterations of the genetic disorder classifier;

input the at least one biological index and the at least one genetic marker into the genetic disorder classifier;

classify, using the trained genetic disorder classifier, the at least one biological index and the at least one genetic marker to a genetic disorder which comprises:

receiving a predisposition index comprising a biological entity in at least a body fluid which indicates a likelihood of a disease; and classifying the at least one genetic marker to the genetic disorder as a function of the predisposition index; and produce a homeopathic program as a function of the genetic disorder, wherein producing the homeopathic program further comprises:

receiving a homeopathic guideline; and producing the homeopathic program as a function of the homeopathic guideline and the genetic disorder utilizing a homeopathic machine-learning model which comprises:

receiving homeopathic training data, wherein the homeopathic training data correlates a plurality of homeopathic guidelines to a plurality of genetic disorder;

training, iteratively, a homeopathic machine-learning model using the homeopathic training data, wherein training the homeopathic machine-learning model includes retraining the homeopathic machine-learning model with feedback from previous iterations of the homeopathic machine-learning model; and generating the homeopathic program as a function of the trained homeopathic machine-learning model, wherein the homeopathic program comprises at least a treatment goal designed to reverse the genetic disorder comprising at least a recommendation of edible supplementation.

2. The system of claim 1, wherein the genetics test data includes a user body measurement.

3. The system of claim 1, wherein the homeopathic program includes a sustenance plan.

4. The system of claim 1, wherein receiving the homeopathic guideline further comprises obtaining a homeopathic input.

5. The system of claim 1, wherein the homeopathic program includes an epigenetic goal.

6. The system of claim 1, wherein the homeopathic program includes a mitigation goal.

7. The system of claim 1, wherein producing the homeopathic program further comprises:

determining a genetic locus; and producing the homeopathic program as a function of the genetic locus.

8. The system of claim 1, wherein producing the homeopathic program further comprises determining an inheritance element.

9. A method for producing a homeopathic program for managing genetic disorders, the method comprising:

receiving, by a computing device, at least one genetic marker and an input comprising genetics test data;

identifying, by the computing device, a plurality of biological indices of a disease state as a function of the genetics test data, wherein the plurality of biological indices comprises at least one biological index related to a genetic disease state;

generating, by the computing device, a genetic disorder classifier, wherein the generating the genetic disorder classifier comprises:

receiving genetic disorder training data, wherein the genetic training data correlates biological indices of genetic disorders and genetic markers to genetic disorder labels; and training, iteratively, the genetic disorder classifier using the genetic disorder training data, wherein training the genetic disorder classifier includes retraining the genetic disorder classifier with feedback from previous iterations of the genetic disorder classifier;

inputting, by the computing device, the at least one biological index and the at least one genetic marker into the genetic disorder classifier;

classifying, by the computing device, using the trained genetic disorder classifier, the at least one biological index and the at least one genetic marker to a genetic disorder which comprises:

receiving a predisposition index comprising a biological entity in at least a body fluid which indicates a likelihood of a disease; and classifying the at least one genetic marker to the genetic disorder as a function of the predisposition index; and producing, by the computing device, a homeopathic program as a function of the genetic disorder, wherein producing the homeopathic program further comprises:

receiving a homeopathic guideline; and producing the homeopathic program as a function of the homeopathic guideline and the genetic disorder utilizing a homeopathic machine-learning model which comprises:

receiving homeopathic training data, wherein the homeopathic training data correlates a plurality of homeopathic guidelines to a plurality of genetic disorder;

training, iteratively, a homeopathic machine-learning model using the homeopathic training data, wherein training the homeopathic machine-learning model includes retraining the homeopathic machine-learning model with feedback from previous iterations of the homeopathic machine-learning model; and generating the homeopathic program as a function of the trained homeopathic machine-learning model, wherein the homeopathic program comprises at least a treatment goal designed to reverse the genetic disorder comprising at least a recommendation of edible supplementation.

10. The method of claim 9, wherein the genetics test data includes a user body measurement.

11. The method of claim 9, wherein the homeopathic program includes a sustenance plan.

12. The method of claim 9, wherein receiving the homeopathic guideline further comprises obtaining a homeopathic input.

13. The method of claim 9, wherein the homeopathic program includes an epigenetic goal.

14. The method of claim 9, wherein the homeopathic program includes a mitigation goal.

15. The method of claim 9, wherein producing the homeopathic program further comprises:

determining a genetic locus; and producing the homeopathic program as a function of the genetic locus.

16. The method of claim 9, wherein producing the homeopathic program further comprises determining an inheritance element.

* * * * *